(12) United States Patent  
Agrawal

(10) Patent No.: US 8,936,569 B2  
(45) Date of Patent: *Jan. 20, 2015

(54) SELF-LOCKING, SELF-BLUNTING SAFETY NEEDLE SYSTEM AND SYRINGE

(76) Inventor: Arpita Agrawal, Chicago, IL (US)

( * ) Notice: Subject to any disclaimer, the term of this patent is extended or adjusted under 35 U.S.C. 154(b) by 1662 days.

This patent is subject to a terminal disclaimer.

(21) Appl. No.: 11/991,114

(22) PCT Filed: Aug. 24, 2006

(86) PCT No.: PCT/US2006/033113  
§ 371 (c)(1),  
(2), (4) Date: Feb. 27, 2008

(87) PCT Pub. No.: WO2007/027507  
PCT Pub. Date: Mar. 8, 2007

(65) Prior Publication Data  
US 2009/0275891 A1  Nov. 5, 2009

Related U.S. Application Data

(60) Provisional application No. 60/713,124, filed on Aug. 31, 2005.

(51) Int. Cl.  
*A61M 5/00* (2006.01)  
*A61M 5/32* (2006.01)  
(Continued)

(52) U.S. Cl.  
CPC .............. *A61M 5/321* (2013.01); *A61M 5/158* (2013.01); *A61M 5/3129* (2013.01); *A61M 2005/3212* (2013.01)  
USPC ....................................................... 604/110

(58) Field of Classification Search  
USPC ............................. 604/110, 164.01, 164.08, 604/165.01–165.03, 239, 263, 272, 170.01, 604/170.02; 600/562, 566, 567, 583; 606/167, 181, 184  
See application file for complete search history.

(56) References Cited

U.S. PATENT DOCUMENTS 1,654,905 A   1/1928  Voos  
3,478,937 A  11/1969  Solowey  
(Continued)

FOREIGN PATENT DOCUMENTS

CN   1547493   11/2004  
RU   2217175   11/2003  
(Continued)

OTHER PUBLICATIONS

International Search Report issued by the WIPO International Bureau in counterpart PCT Application No. PCT/US2006/033113 on Jul. 3, 2007.

(Continued)

*Primary Examiner* — Nathan R Price

(57) ABSTRACT

A safety needle locking device, which may be used with a syringe, consisting of a Blunting Member (19). The Needle (16) has a Needle Curvature (25) which allows locking of the Blunting Member (19) within the needle with the indent (27). The blunting member also has a Puncture Tip Protector (26) which allows for the Needle Tip (24) to be sheathed upon expulsion of the fluid. The needle is tubular with one surface flattened out. The Blunting Member is aligned within the needle. When the fluids are expelled the blunting member moves out, blocks the needle tip and locks inside the needle. Thus preventing reuse and needle stick injury. The syringe is flattened along one longitudinal surface to allow for alignment.

16 Claims, 10 Drawing Sheets

(51) Int. Cl.
*A61M 5/158* (2006.01)
*A61M 5/31* (2006.01)

(56) References Cited

U.S. PATENT DOCUMENTS

| | | | |
|---|---|---|---|
| 3,885,562 A * | 5/1975 | Lampkin | 604/189 |
| 3,982,546 A | 9/1976 | Friend | |
| 4,131,978 A | 1/1979 | Zocher | |
| 4,233,975 A | 11/1980 | Yerman | |
| 4,790,329 A * | 12/1988 | Simon | 600/562 |
| 4,828,547 A | 5/1989 | Sahi et al. | |
| 4,892,107 A | 1/1990 | Haber | |
| 5,423,410 A | 6/1995 | Zielke | |
| 5,423,760 A | 6/1995 | Yoon | |
| 5,556,410 A * | 9/1996 | Mittermeir et al. | 606/185 |
| 5,993,418 A | 11/1999 | Alexander | |
| 6,419,658 B1 | 7/2002 | Restelli | |
| 6,436,068 B1 * | 8/2002 | Bardy | 604/57 |
| 6,585,702 B1 | 7/2003 | Brunel | |
| 6,733,465 B1 | 5/2004 | Smutney | |
| 6,814,707 B2 | 11/2004 | Collins | |
| 7,731,692 B2 * | 6/2010 | Moos et al. | 604/164.08 |
| 8,608,692 B2 * | 12/2013 | Agrawal | 604/110 |
| 2003/0093098 A1 | 5/2003 | Heitzmann | |
| 2005/0015058 A1 | 1/2005 | Millerd | |
| 2005/0027263 A1 | 2/2005 | Woehr et al. | |
| 2007/0016142 A1 | 1/2007 | Burren | |
| 2010/0036316 A1 | 2/2010 | Agrawal | |

FOREIGN PATENT DOCUMENTS

| | | |
|---|---|---|
| RU | 2220747 | 10/2004 |
| WO | 03/011381 | 2/2003 |

OTHER PUBLICATIONS

Written Opinion issued by the WIPO International Bureau in counterpart PCT Application No. PCT/US2006/033113 on Jul. 3, 2007.
Information Disclosure Statement submitted in U.S. Appl. No. 12/450,262, received by the US Patent and Trademark Office on Sep. 17, 2009.
International Search Report issued by the WIPO International Bureau in PCT Application No. PCT/US2009/003647 (counterpart to U.S. Appl. No. 12/450,262) on Sep. 25, 2008.
Written Opinion issued by the WIPO International Bureau in PCT Application No. PCT/US2009/003647 (counterpart to U.S. Appl. No. 12/450,262) on Sep. 25, 2008.
International Preliminary Report on Patentability issued by the WIPO International Bureau in PCT Application No. PCT/ US2009/ 003647 (counterpart to U.S. Appl. No. 12/450,262) on Sep. 22, 2009.

* cited by examiner

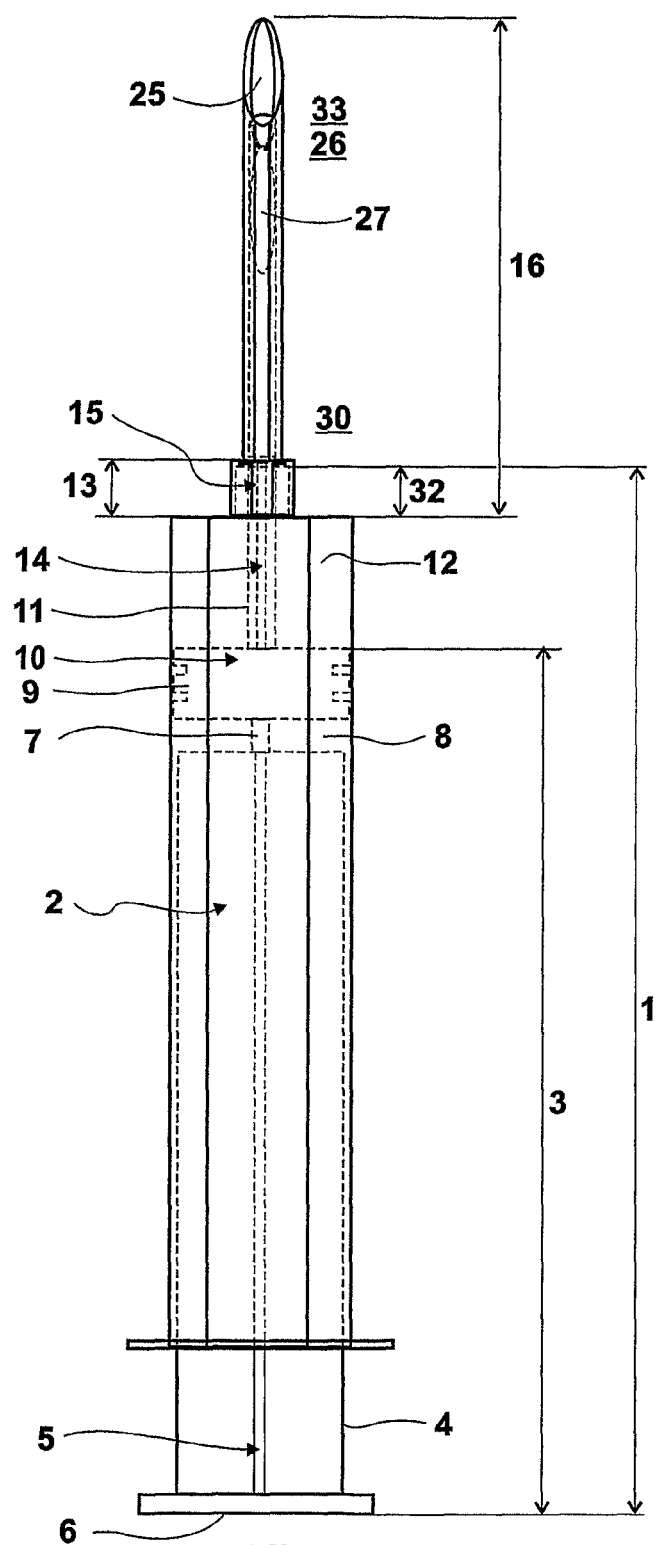
Fig.1.1

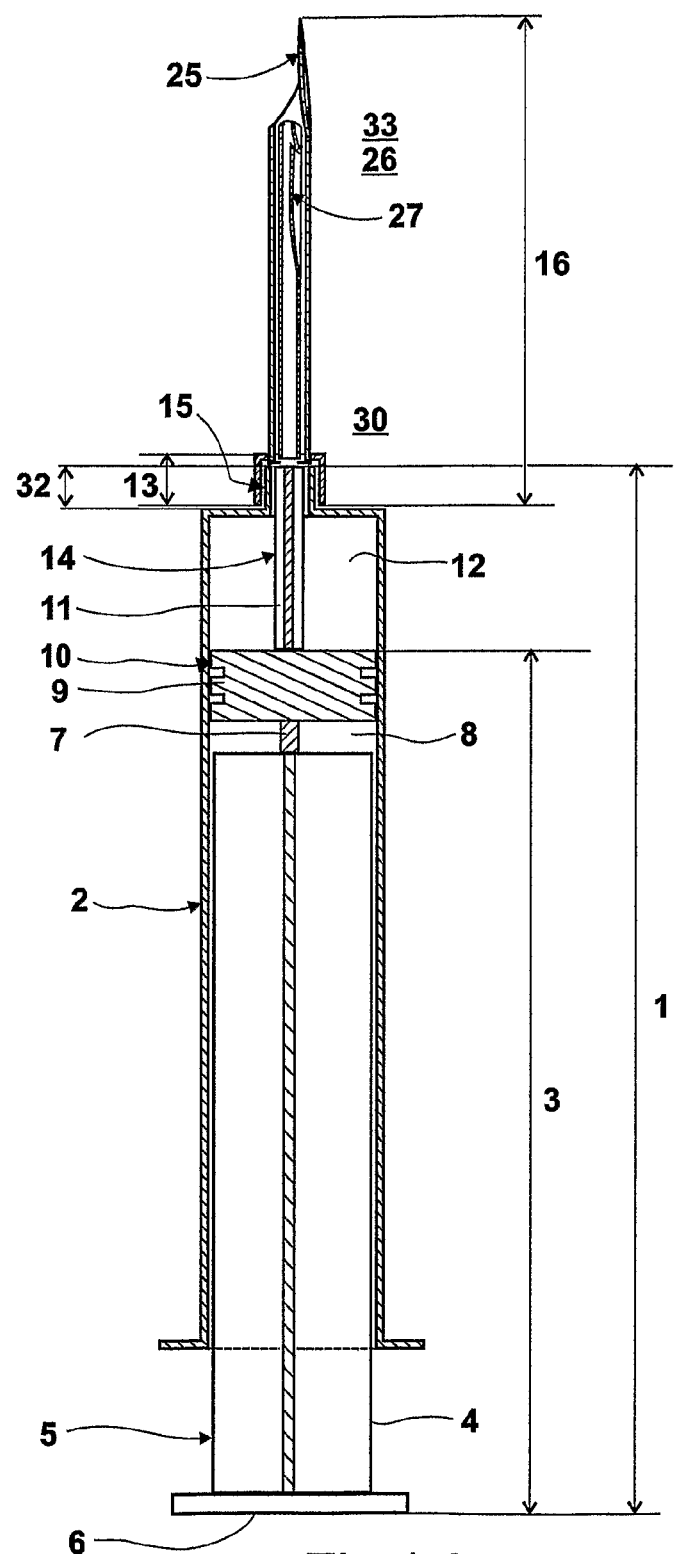
Fig.1.2

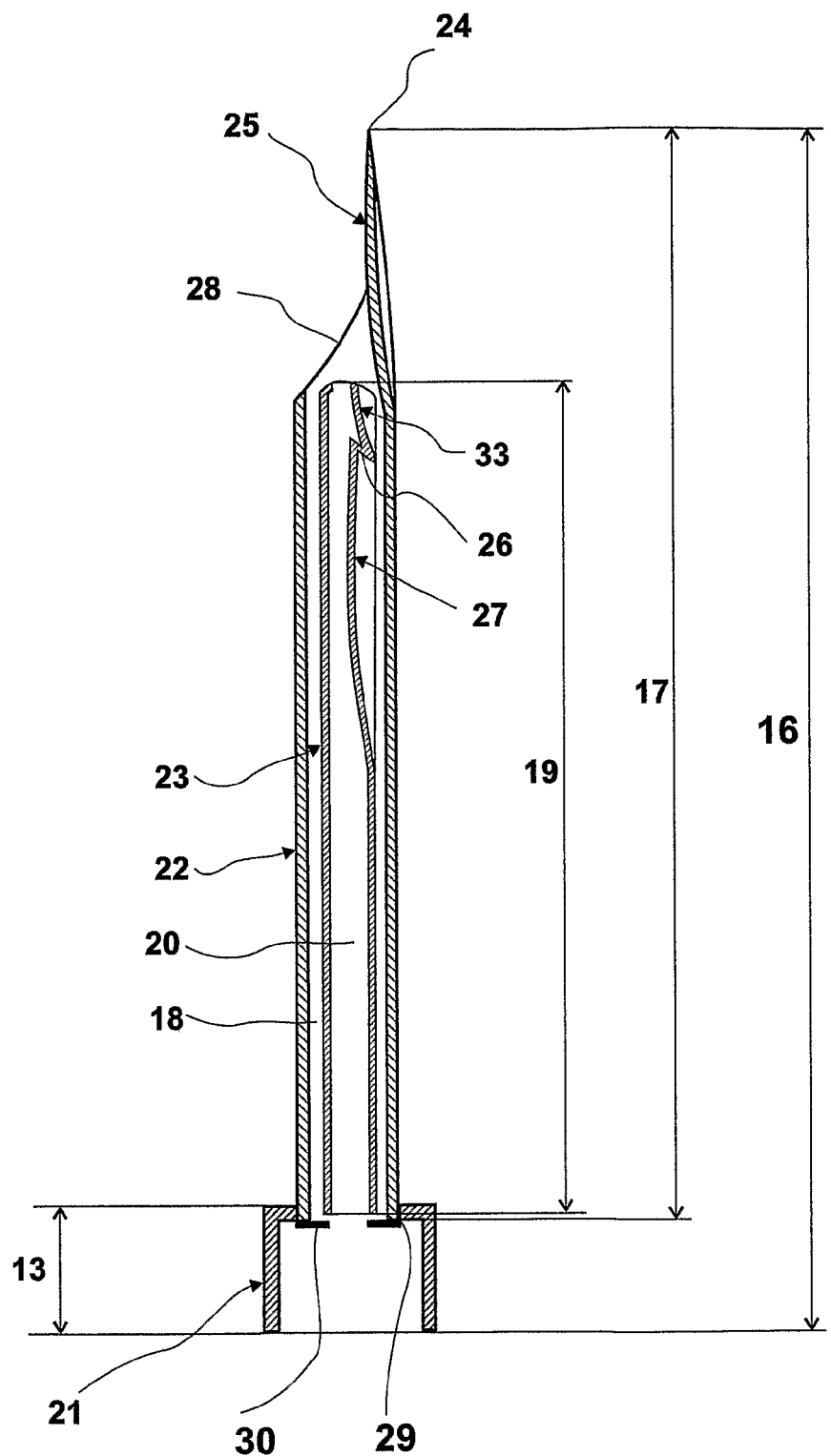
Fig.1.3

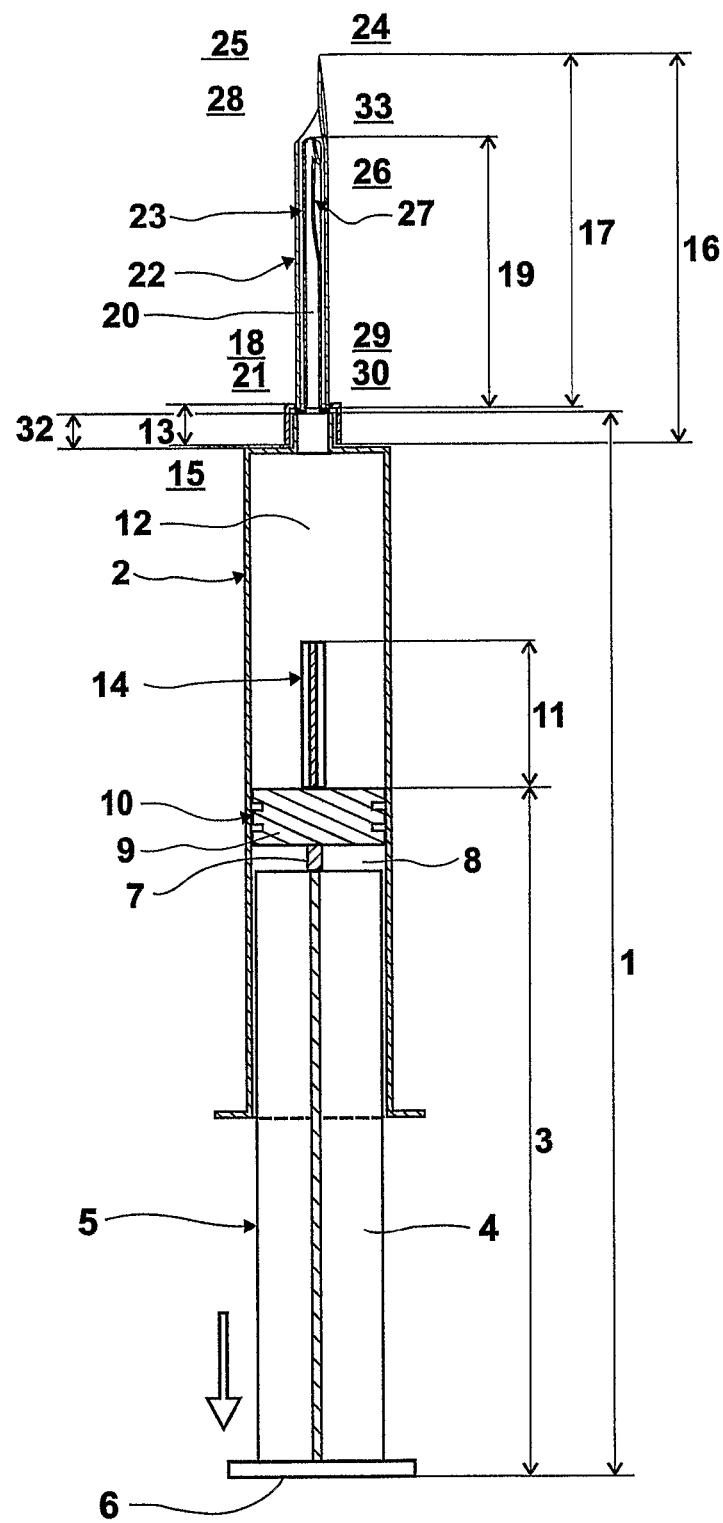
Fig. 2.1

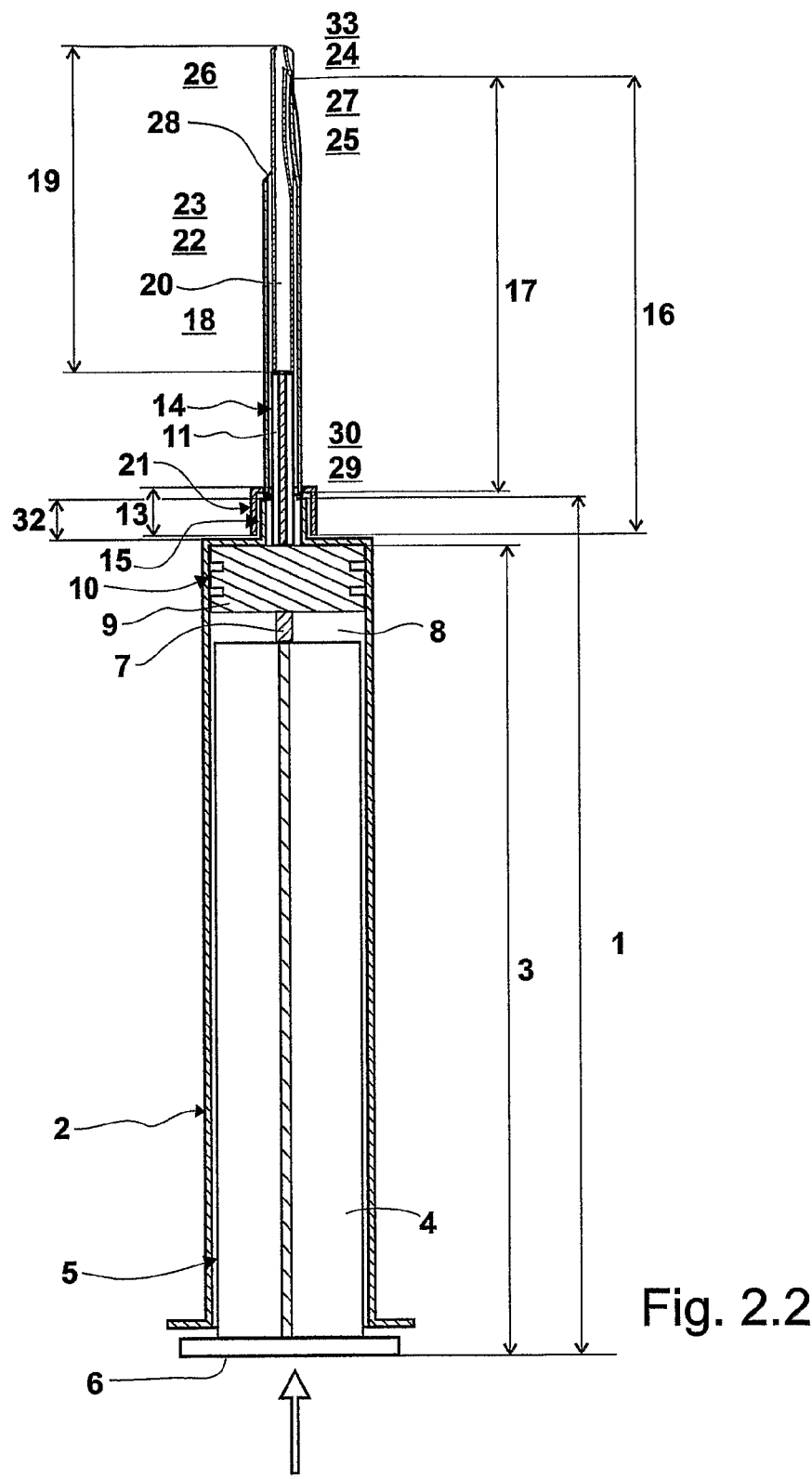
Fig. 2.2

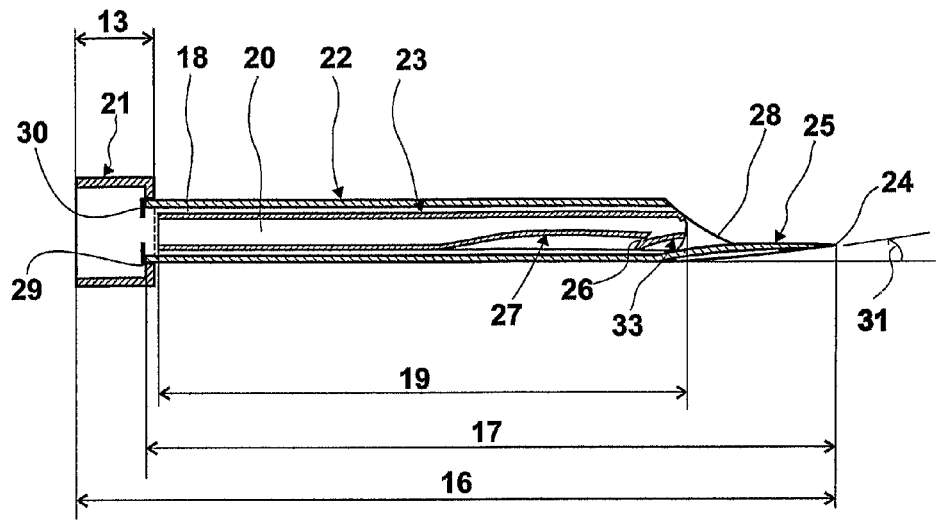
Fig. 3.1
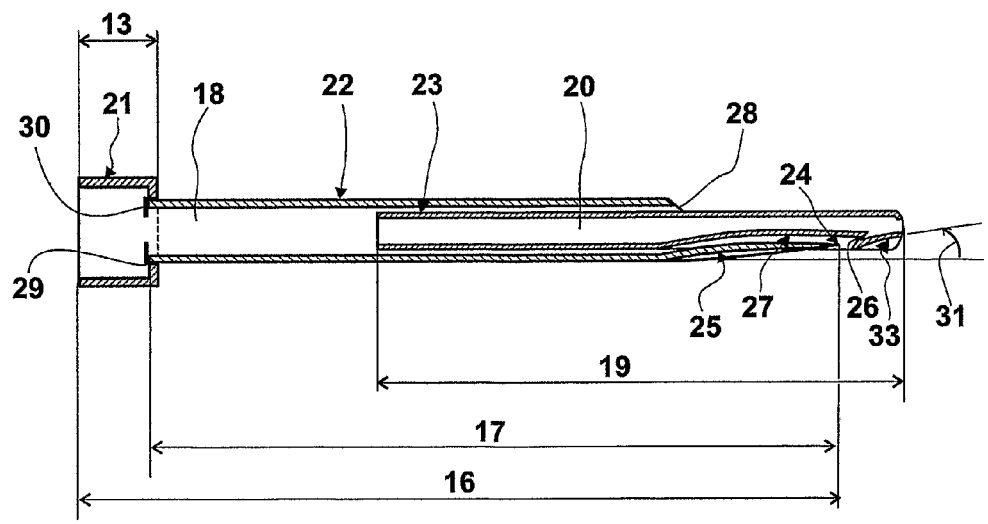
Fig. 3.2

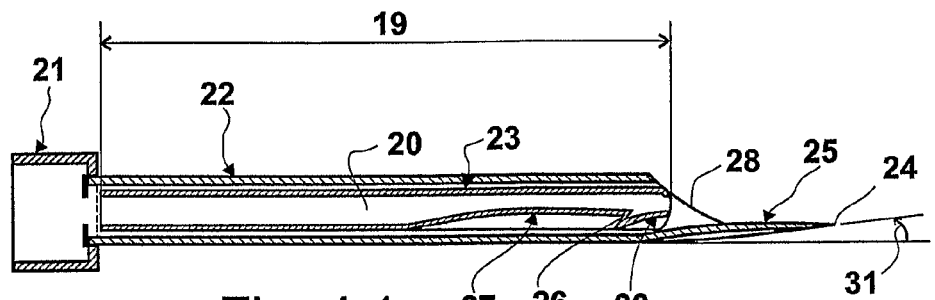
Fig. 4.1
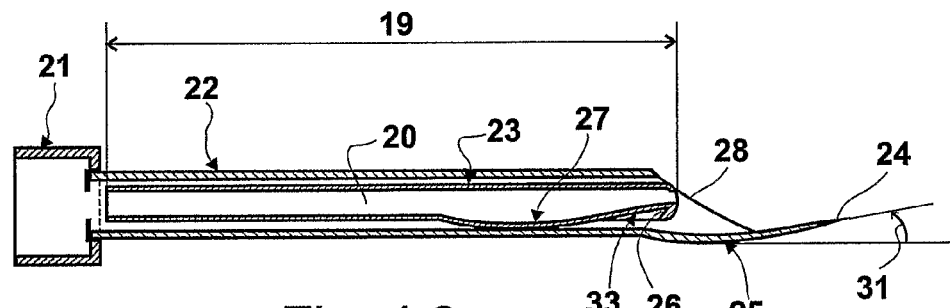
Fig. 4.2
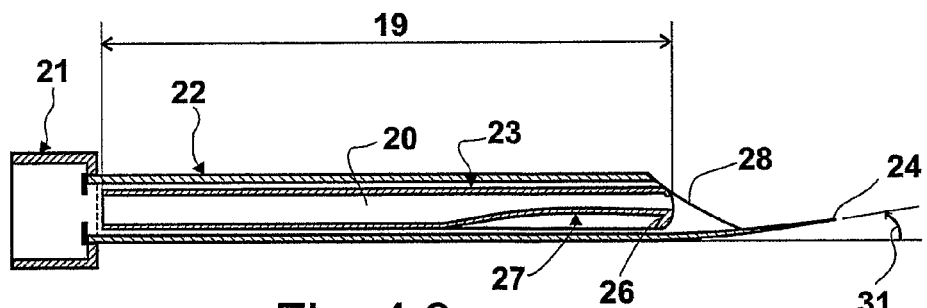
Fig. 4.3

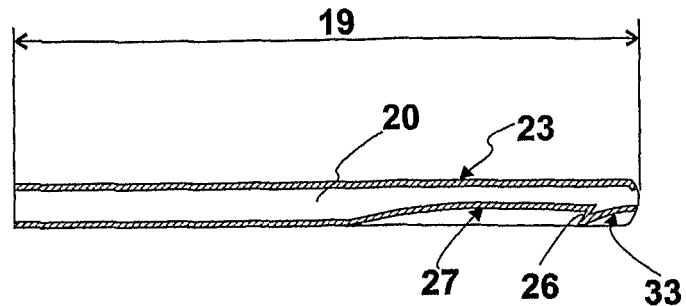
Fig.5.1
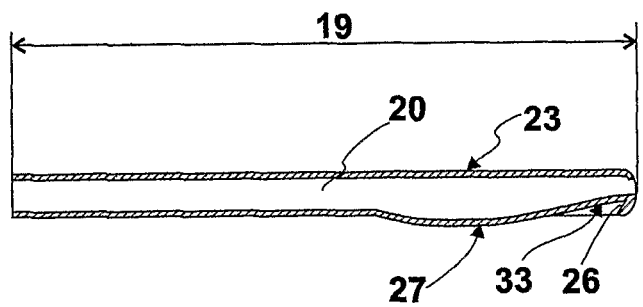
Fig.5.2
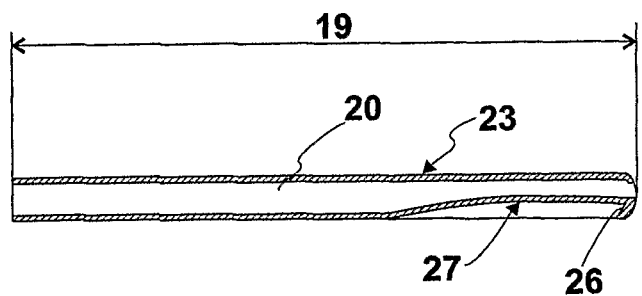
Fig.5.3

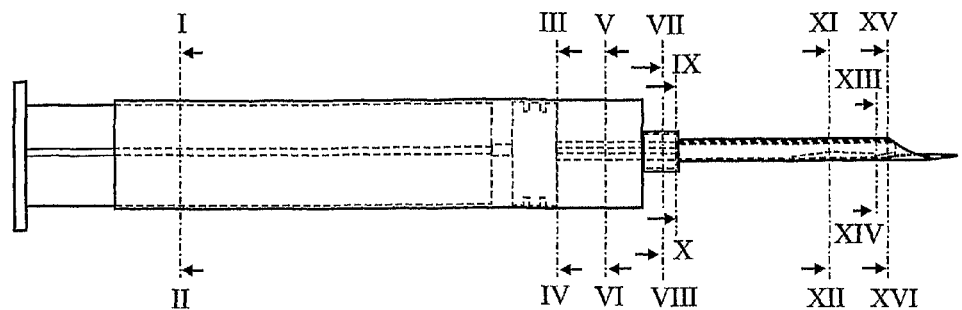
Fig.6.1
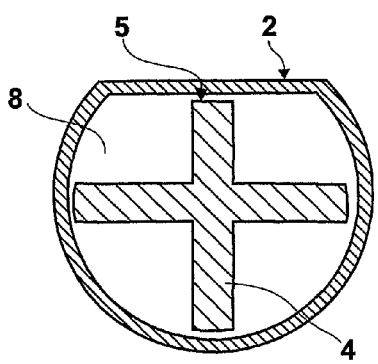
Section on I-II
Fig.6.2
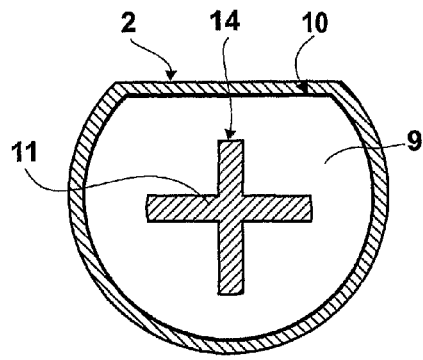
Section on III-IV
Fig.6.3
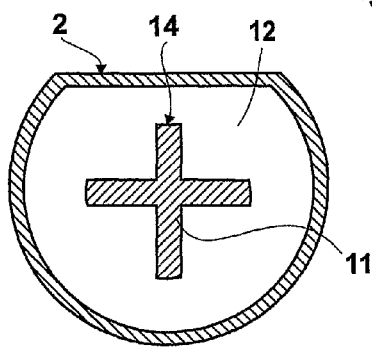
Section on V-VI
Fig.6.4

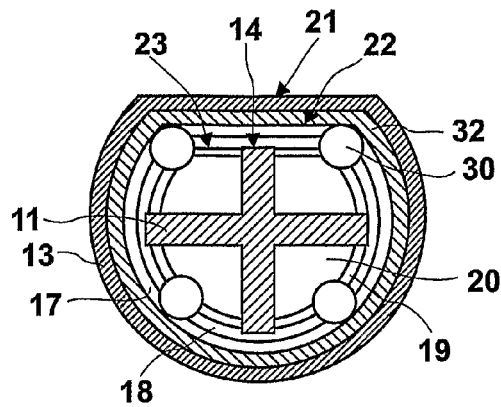
Section on VII-VIII
Fig.6.5
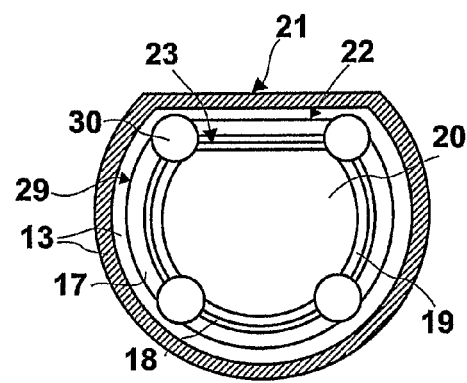
Section on IX-X
Fig.6.6
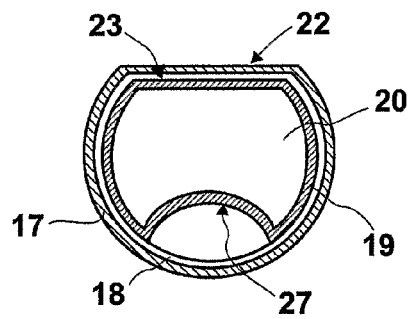
Section on XI-XII
Fig.6.7
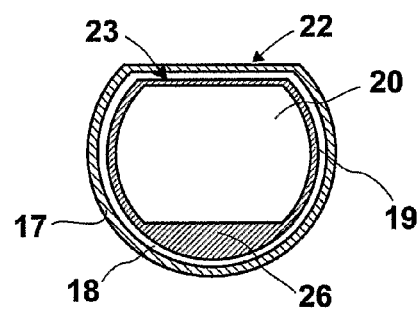
Section on XIII-XIV
Fig.6.8
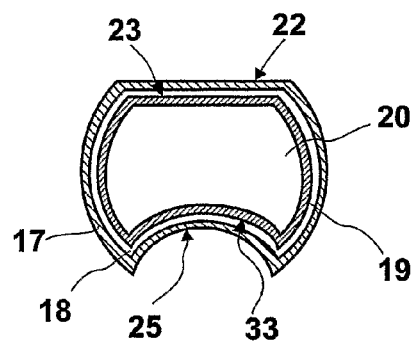
Section on XV-XVI
Fig.6.9

ововInternetSELF-LOCKING, SELF-BLUNTING SAFETY
NEEDLE SYSTEM AND SYRINGE

CROSS-REFERENCE TO RELATED
APPLICATIONS

This is a Section 371 National Stage application based on PCT International Application No. PCT/US2006/033113, filed on Aug. 24, 2006, claiming priority from U.S. Provisional Patent Application No. 60/713,124 filed on Aug. 31, 2005.

STATEMENT REGARDING FEDERALLY
SPONSORED RESEARCH OR DEVELOPMENT

Not applicable.

NAMES OF PARTIES TO A JOINT RESEARCH
AGREEMENT

Not applicable.

INCORPORATION BY REFERENCE OF
MATERIAL SUBMITTED ON A COMPACT DISC

Not applicable.

BACKGROUND OF THE INVENTION

1. Field of the Invention

The invention relates to a needle which may be used with a hypodermic syringe, IV Catheter, and for any medical or industrial purpose. The needle is a self blunting instrument which upon use will prevent needle stick injuries.

2. Background

The present invention has been made to protect the health of medical and non-medical persons who face the potential risk of needle stick injury. Although syringes and needles have been widely used in the medical field or industry for over a hundred years, their potential hazardous nature and their implications on health care and other workers have only recently been studied. Safety-Engineered Medical Devices (SEMDs) are specially manufactured versions of these sharp and potentially injurious medical products, designed for safer use by medical professionals.

The world market for SEMD's totaled an estimated $780 Million in the year 2001 alone and is projected to exceed to $1.6 billion by 2005, based on 20% predicted growth. There are approximately 800,000 to 1 Million exposures to blood borne pathogens in US every year due to needle stick injuries. Of which approximately 2% are HIV exposures resulting in 16,000 new infections. More than 20 diseases can be transmitted due to Needle Stick Injuries like AIDS, Hepatitis B and Hepatitis C exposures.

BRIEF SUMMARY OF THE INVENTION

It is the objective of the present invention to provide a self-blunting needle which prevents accidental, inadvertent contact with the Needle Puncture Tip during and after use, with a view to prevent needle stick injury. It is also the objective of the present invention to create a self blunting needle with a lock. The needle's blunting and safety feature does not require additional human action for activation. The safety feature gets automatically activated.

The needle is safe during and after use, the safety feature being an integral part of the design. The intention is to create a simple low cost self blunting needle which does not require human action to activate the safety feature. The invention requires no additional learning or training by the medical or non-medical staff for the activation of the safety feature.

Furthermore, the objective of the present invention is to create a self blunting needle which is both inexpensive and practical in making thus ensuring production on a commercial scale.

BRIEF DESCRIPTION OF THE SEVERAL
VIEWS OF THE DRAWINGS

FIG. 1.1 is a complete view of the needle system and syringe, at shipping position.

FIG. 1.2 is a length wise cross section view of the hypodermic syringe with the needle.

FIG. 1.3 is the length wise cross section view of the needle.

FIG. 2.1 is the length wise cross section view of the needle during the hypodermic syringe use, at the stage of the intake of fluid.

FIG. 2.2 is the length wise cross section view of the needle during the hypodermic syringe use. This is the view of the needle after fluid is expelled.

FIG. 3.1 is the length wise cross section view of the needle with the Blunting Member inside at shipping position.

FIG. 3.2 is the length wise cross section view of the needle with the Blunting Member inside it after use.

FIG. 4.1 is a cross section view of the needle and the Blunting Member with two inward curvatures in shipping position.

FIG. 4.2 is a length wise cross section view of the needle and the blunting instrument with an outward curvature at shipping position.

FIG. 4.3 shows a length wise cross section view of the needle with the Blunting Member and Puncture Tip Protector.

FIG. 5.1 is a length wise cross section view of the blunting instrument.

FIG. 5.2 is a length wise cross section view of an alternative method.

FIG. 5.3 shows a Blunting Member with an inward indent and a Puncture Tip Protector.

FIG. 6.1 shows the cross sections marked on the syringe and needle with Blunting Member.

FIG. 6.2 shows the cross section at I-II with reference to FIG. 6.1.

FIG. 6.3 shows the cross section at III-IV with reference to FIG. 6.1.

FIG. 6.4 shows the cross section at V-VI with reference to FIG. 6.1.

FIG. 6.5 shows the cross section at VII-VIII with reference to FIG. 6.1.

FIG. 6.6 shows the cross section at IX-X with reference to FIG. 6.1.

FIG. 6.7 shows the cross section at XI-XII with reference to FIG. 6.1.

FIG. 6.8 shows the cross section at XIII-XIV with reference to FIG. 6.1.

FIG. 6.9 shows the cross section at XV-XVI with reference to FIG. 6.1.

DETAILED DESCRIPTION OF THE INVENTION

Best Mode for Carrying Out the Invention

FIG. 1.1 is a complete view of the needle system and syringe. Referring now to the drawing in FIG. 1.2 which presents a hypodermic syringe generally represented at 1.

Unlike a typical tubular syringe, the syringe has a flattened surface along the length represented at 2. The Plunger Rod is generally indicated at 3, the Plunger Rod shall have a normal arm at 4 and a Flattened arm at 5, to align with the flattened surface of the Tubular Syringe at 2. The Plunger Rod has a thumb rest at 6.

The plunger arms extend into a plunger head support at 7. There is a cavity 8 between the plunger arms and the plunger head 9. The plunger head 9 has a flattened surface 10 to align with the flattened surface of the syringe 2. From the Plunger Head 9 emerges Plunger Extension 11 into the syringe cavity 12. Plunger extension 11 extends to the Needle Mouth that is generally indicated at 13.

The Plunger Extension 11 has a flattened surface 14 along the length. The Plunger Extension can be of any shape that allows alignment along with the flow of fluids. FIG. 1.3 is a length wise cross section view of the Needle 16 consisting of the Needle Mouth 13 and Needle Tube 17 and Needle Blunting Member 19. For the flow of fluids the Needle Tube 17 has a Needle Cavity 18 and the Blunting Member 19 has Blunting Member Cavity 20. Instead of the typical tubular needle, the Needle Mouth 13, the Needle Tube 17 and the Blunting Member 19 have a flattened surface along the length at 21, 22, 23 respectively, to allow for alignment.

The Needle Mouth 13 when affixed to the Syringe Head 15, as represented in FIG. 1.1 brings the Blunting Member 19 in alignment with the Plunger extension 11. The Needle Puncture Tip 24 has small inward or outward curvature 25. The Needle Puncture Tip 24 extends at an angle upward as detailed in FIG. 3.1 at 31. The Blunting Member 19 has two indents. The Second Indent 33 allows for the Blunting Member to smoothly glide over the Needle Curvature 25.

The First Indent 27 is curved to correspond with the curvature in the needle 25. When the Blunting Member 19 is completely extended the First Indent 27 will sheath the Puncture Tip 24 of the Needle 16. The Puncture tip 24 of the needle is covered by the Puncture Tip Protector 26.

The Blunting Member 19 can be of any shape, or there may be a transition in the shape which allows for the free flow of fluids. The aim of the aforementioned shapes is alignment, flow of fluids and locking inside the Needle Tube 17. When the fluid is expelled the Plunger Extension 11 pushes out the Blunting Member 19. A Needle Mouth Stopper 30, in FIGS. 1.3, 3.1 and 3.2 has been detailed. The Needle Mouth Stopper 30 is positioned at 29—the point of intersection of the Needle Mourn 13 and Needle Tube 17. The device is in the form of ridges that stop the Blunting Member 19 from falling out of the needle.

FIG. 2.1 shows the needle during intake of fluid. When the Plunger Rod 3 is pulled back the Plunger Extension 11 also gets pulled back, the fluid enters from the Needle Opening 28 through the Blunting Cavity 20 and the Needle Cavity 18 in the Needle Tube 17. The Blunting Member remains in a retracted position as it is blocked with Stopper 30.

FIG. 2.2 shows when the needle is expelling or has expelled the fluid. The Plunger Rod 3 is pushed into the syringe; this in turn pushes the Plunger Extension 11 into the Syringe Head 32. The Plunger Extension 11 pushes the Blunting Member 19 outwards from the Needle Mouth Stopper 30. The Blunting Member gets extended when the fluid is expelled. When the fluid is being expelled the Second Indent 33 would glide over the Needle Curvature 25.

The First Indent 27 would sheath the Needle Puncture Tip 24 and get locked in place by the Needle Curvature 25. The Needle Puncture Tip is covered by the Puncture Tip Protector at 26 so that the Puncture Tip is not exposed. In FIG. 4.2 shows the Needle with an outward curvature at 25, this corresponds with the Blunting Members outward indent at 27. When the fluid is expelled the Outward Indent of the Blunting Member at 27 gets locked into me outward curvature of the needle at 25. The Puncture Tip Protector at 26 covers the Needle Puncture Tip 24. FIG. 4.3 the Blunting Member has only one indent at 27 to sheath the tip of the needle and the Puncture Tip Protector at 26. In FIGS. 4.1, 4.2 and 43 the Needle Puncture Tip 24 is at a slight angle 31.

When the fluid is completely expelled the Blunting Member gets extended outwards. The Blunting Member indent at 27 then sheaths the Needle Puncture Tip 24 which gets locked in because of its angular structure. The Puncture Tip Protector at 26 covers the Needle Puncture Tip 24. The Needle Tube 16, the Blunting Member 19, the Needle Mouth 13, though typically tubular have a flattened surface along the length for alignment at 21, 22 and 23 respectively.

DESCRIPTION OF DRAWINGS

FIG. 1.1 is a complete view of the hypodermic syringe with needle, at shipping position. FIG. 1.2 is the length wise cross section view of the hypodermic syringe with the needle. FIG. 1.3 is the length wise cross section view of the needle. FIG. 2.1 is the length wise cross section view of the needle during the hypodermic syringe use, at the stage of the intake of fluid.

FIG. 2.2 is the length wise cross section view of the needle during the hypodermic syringe use. This is the view of me needle after fluid is expelled. FIG. 3.1 is the length wise cross section view of the needle with the Blunting Member inside at shipping position. FIG. 3.2 is the length wise cross section view of the needle with the Blunting Member inside it after use. FIG. 4.1 is a cross section view of the needle and the Blunting Member with two inward curvatures at 27 and 33 in shipping position. The Puncture Tip of the needle is at an angle. FIG. 4.2 is a length wise cross section view of the needle and the blunting instrument with an outward curvature at shipping position. The Blunting Member has an outward indent at 27 and a inward indent at 33 which juts out to form Puncture Tip Protector at 26. The Puncture Tip of the needle is at an angle.

FIG. 4.3 has an inward indent at 27 and the Blunting Member juts out to form the Puncture Tip Protector at 26. The Puncture Tip of the needle is at an angle. FIG. 5.1 is a length wise cross section view of the blunting instrument wherein the blunting member has two inward curvatures, one which locks the blunting member and sheaths the puncture tip. The other allows for smooth movement of the Blunting Member.

FIG. 5.2 is a length wise cross section view of an alternative method wherein the blunting instrument's blunting edge has an outward indent and an inward indent with a Puncture Tip Protector 26. The outward indent locks the blunting member in place and the inward indent sheaths the puncture tip. FIG. 5.3 shows a Blunting Member with an inward indent at 27 and an Puncture Tip Protector at 26. After expulsion of the fluid, the inward indent 27 sheaths the Needle Tip, the Puncture Tip Protector 26 covers the tip and gets locked in place. FIG. 6.1 shows the cross sections marked on the syringe and needle with Blunting Member. FIG. 6.2 shows the cross section at I-II with reference to FIG. 6.1.

FIG. 6.3 shows the cross section at III-IV with reference to FIG. 6.1. FIG. 6.4 shows the cross section at V-VI with reference to FIG. 6.1. FIG. 6.5 shows the cross section at VII-VIII with reference to FIG. 6.1. FIG. 6.6 shows the cross section at IX-X with reference to FIG. 6.1. FIG. 6.7 shows the cross section at XI-XII with reference to FIG. 6.1. FIG. 6.8 shows the cross section at XIII-XIV with reference to FIG. 6.1. FIG. 6.9 shows the cross section at XV-XVI with reference to FIG. 6.1

The points of reference in all the figures is the same from FIG. 1.1 to FIG. 5.3 FIG. 1.2 shows a Hypodermic Syringe indicated generally at 1. The semi-tubular syringe has a flattened surface along the Length at 2. The Plunger Rod has been generally indicated at 3. The Plunger Rod 3 has a Normal Arm at 4 and a Flattened Plunger Arm at 5. The Flattened Plunger Arm has been flattened to align with the flattened surface of the syringe 2.

A Thumb Rest has been provided at 6. The Plunger Rod 3 extends into a Plunger Head Support at 7. A cavity is created between the Plunger Arms and the Plunger Head 9, at 8. The Plunger Head 9 has a flattened surface at 10 to align with the flattened surface of the Syringe 2. The Plunger Head 9 is aligned and attached to the Plunger Extension at 11. Between the Plunger Head 9 and the Syringe Head 32 is the Syringe Cavity 12. Syringe Cavity 12 is where the fluid collects during the intake of fluids. The Plunger Extension and the Syringe Head are flattened at 14 and 15 respectively for alignment.

FIG. 1.3 depicts a needle generally at 16. The needle consists of Needle Mouth 13, Needle Tube 17 and Blunting Member 19 which have a flattened surface along the length at 21, 22 and 23 respectively. There is a Needle Cavity at 18 and a Blunting Member Cavity at 20.

The Needle Puncture Tip at 24 is at a slight angle as depicted at 31 and further clearly marked out in FIG. 3.1. There is a slight curvature in the needle at 25. The Needle Curvature 25 can be either inward or outward. The Blunting Member 19 has the First Indent at 27 and the Second Indent at 33 in FIG. 3.1. The Blunting Member juts out to form a Puncture Tip Protector at 26. The Needle Opening is depicted at 28. 29 is where the Needle Mouth and Needle Tube touch or join, 30 is the Needle Mouth Stopper, cross section of which is depicted in FIGS. 6.5 and 6.6.

In FIG. 6.1 a syringe at shipping position has been depicted with the points at which the cross sections have been drawn. FIG. 6.2 is the cross Section at I-II of the syringe. 2 is the flattened surface along the Syringe Length. 4 is the Normal Plunger Arm and 5 is the Flattened Plunger Arm. 8 is the Syringe Cavity before the Plunger Head. In FIG. 6.3 cross section of the Syringe at III-IV is generally depicted. 9 is the Plunger head, 11 is the Plunger Extension. 2 is the flattened surface along the Tubular Syringe Length. 10 is the flattened surface of the Syringe Head.

14 is the Flattened surface of the Plunger Extension. FIG. 6.4 cross section V-VI is generally depicted. 11 is the Plunger Extension with the flattened surface at 14. 12 is the Syringe Cavity for the fluid. 2 is the Flattened surface along the length of the syringe. FIG. 6.5 is the cross section of the Syringe at VII-VIII. 17 is the Needle Tube. 11 is the Plunger Extension with a flattened surface at 14. 19 is the Blunting Member. 20 is the cavity in the Blunting Member. 23 is the flattened surface of the Blunting Member 19. 22 is the Flat Surface of the Needle Tube 17. 30 is the Needle Mouth Stopper which prevents the Blunting Member from falling out of the Needle Tube.

There is a Needle Cavity at 18. 32 is the Syringe Head and 13 is the needle mouth. FIG. 6.6 is the cross section generally depicted at IX-X. All the parts are the same as in FIG. 6.6 except where that Plunger Extension 11 and the Syringe Head at 32 can no more be seen and the Blunting Member 19 is seen. In FIG. 6.7 the cross section of the needle at XI-XII is generally depicted.

An increase in the Cavity at 18 is created in the needle due to the First Indent 27 of the Blunting Member 19. In FIG. 6.8 cross section at XIII-XIV is generally depicted. Blunting Member 19 and the Needle Tube 17 have no curvature and are tubular, except for the flattened surface 23 and 22. 26 is the Puncture tip Protector. FIG. 6.9 is the cross section of the needle at XV-XVI. 25 is the Needle Curvature and 33 is the Second Indent of the Blunting Member 19 when the Blunting Member is not extended.

DISCLOSURE

The invention relates to a needle which may be used with a hypodermic syringe, IV Catheter, and for any medical or industrial purpose. The needle is a self blunting instrument which upon use will prevent needle stick injuries.

The needle is safe during and after use, the safety feature being an integral part of the design. The intention is to create a simple low cost self blunting needle which does not require human action to activate the safety feature. The invention requires no additional learning or training by the medical or non-medical staff for the activation of the safety feature.

It is the objective of the present invention to provide a self-blunting needle which prevents accidental, inadvertent contact with the Needle Puncture Tip during and after use, with a view to prevent needle stick injury. It is also the objective of the present invention to create a self blunting needle with a lock and a puncture tip protector. The needle's blunting and safety feature does not require additional human action for activation. The safety feature gets automatically activated.

Furthermore, the objective of the present invention is to create a self blunting needle which is both inexpensive and practical in making ensuring production on a commercial scale. Devices of this invention may be employed to inject or withdraw fluids or gases for both medical and non-medical purposes.

The device comprises of the following components. A needle member which terminates in a Needle Puncture Tip. The needle member has a slight inward or outward curvature before it tapers into the Needle Puncture Tip. This inward or outward curvature will lock the Blunting Member in the extended position. Further more the needle puncturing tip will be at a slight angle to facilitate the sheathing of the Needle Puncture Tip.

A Blunting Member, is placed inside the needle member. The Blunting Member can be of any shape as long as it aligns within the needle, allows for the flow of fluids and locks. Upon mechanical application of pressure on the plunger, the Blunting Member extends beyond the mouth of the needle and thus prevents accidental needle stick injury. An internal stopper blocks the Blunting Member from falling back within the needle.

When the fluid gets expelled the Blunting Member gets extended and the sharp point of the needle gets sheathed within the periphery of the Blunting Member.

I claim:
1. A self-locking, self-blunting, single-use fluid transfer device comprising a needle assembly and a syringe assembly, said needle assembly comprising:
   at least one blunting member comprising a first indent and a puncture tip protector; and
   a needle tube comprising a needle mouth, a needle opening, a needle cavity between the needle mouth and the needle opening, a needle curvature and a needle puncture tip, said needle curvature occurring along a part of the needle tube before the needle tube tapers into the needle puncture tip;

wherein said needle curvature corresponds to a curvature of the first indent of said blunting member, and
wherein said blunting member is inside said needle cavity; and said syringe assembly further comprising:
a syringe tube,
a plunger rod having a plunger head, and
a plunger extension;
wherein said plunger head, plunger extension and blunting member are aligned so that when in use said plunger rod is pushed, said plunger rod pushes said plunger extension and said plunger extension pushes said blunting member so that said curvature of said first indent and said puncture tip protector extend out of the needle cavity to lock, cover and sheath said needle curvature and said needle puncture tip.

2. The fluid transfer device of claim 1, wherein said needle puncture tip is angled at the needle opening.

3. The fluid transfer device of claim 1, wherein said needle curvature comprises an inward curvature.

4. The fluid transfer device of claim 1, wherein said needle curvature comprises an outward curvature.

5. The fluid transfer device of claim 1, further comprising a stopper in form of ridges within the needle mouth, wherein said stopper is to prevent said blunting member from falling out of said needle tube.

6. The fluid transfer device of claim 1, wherein said blunting member and said needle tube comprise a uniform or a transition in shape for allowing flow of fluids, alignment and locking within said needle assembly.

7. The fluid transfer device of claim 1, wherein said blunting member and said needle tube each have a flattened surface, and wherein said blunting member and said needle tube are configured to be aligned by these flattened surfaces.

8. The fluid transfer device of claim 1, wherein said plunger extension comprises a flattened surface along its longitudinal length for aligning with at least one of the group consisting of:
a flattened surface of said plunger head;
a flattened surface of said blunting member; and
a flattened surface of said needle mouth.

9. The fluid transfer device of claim 1, wherein said plunger head comprises a flattened surface along its longitudinal length for aligning with a flattened surface of said syringe tube.

10. The fluid transfer device of claim 1, wherein said plunger rod comprises a flattened surface along its longitudinal length for aligning with parts of said syringe assembly.

11. The fluid transfer device of claim 1, further comprising a syringe head where the syringe tube connects the syringe assembly and the needle mouth, wherein said needle mouth has a flattened surface along its longitudinal length and said syringe head has a flattened surface along its longitudinal length, and wherein said flattened surface of the needle mouth is for alignment with said flattened surface of said syringe head.

12. The fluid transfer device of claim 1, wherein the needle puncture tip is sheathed from more than one side by said blunting member.

13. The fluid transfer device of claim 1, wherein the blunting member is positioned to lock, cover and sheath said needle puncture tip and said needle curvature from inside the needle tube.

14. A self-locking, self-blunting, single-use needle system comprising:
a needle assembly comprising:
at least one blunting member comprising a first indent and a puncture tip protector; and
a needle tube comprising a needle mouth, a needle opening, a needle cavity between the needle mouth and the needle opening, a needle curvature and a needle puncture tip, said needle curvature occurring along a part of the needle tube before the needle tube tapers into the needle puncture tip;
wherein said needle curvature corresponds to a curvature of the first indent of said blunting member;
wherein said blunting member is inside said needle cavity; and
wherein when in use said blunting member is to be pushed out of said needle cavity so that said curvature of said first indent and said puncture tip protector lock, cover and sheath said needle puncture tip and said needle curvature.

15. The needle system of claim 14, further comprising a flattened surface on the needle mouth aligned with a flattened surface on a plunger extension part of a syringe assembly.

16. The needle system of claim 14, wherein said blunting member and said needle tube are aligned by a flattened surface of the blunting member and a flattened surface of the needle tube.

* * * * *